United States Patent [19]
Nabel

[11] Patent Number: 5,990,090
[45] Date of Patent: Nov. 23, 1999

[54] METHODS AND COMPOSITIONS FOR TREATMENT OF DISEASES

[75] Inventor: Gary Jan Nabel, Ann Arbor, Mich.

[73] Assignee: The University of Michigan, Mich.

[21] Appl. No.: 08/607,519

[22] Filed: Feb. 27, 1996

Related U.S. Application Data

[63] Continuation of application No. 08/123,188, Sep. 20, 1993, abandoned.

[51] Int. Cl.⁶ .............................. A61K 48/00; C07H 21/04
[52] U.S. Cl. ............................................... 514/44; 536/24.5
[58] Field of Search .............................. 514/44; 536/24.5, 536/23.1

[56] References Cited

FOREIGN PATENT DOCUMENTS 9111535  8/1991  WIPO .

OTHER PUBLICATIONS

Stull et al (1995) Pharmaceutical Research 12:465–483.

Bielinska et al (1990) Science 250:997–1000.

Schreck et al. (1991) EMBO J 10:2247–2258.

N Mukaida et al (1990) J Biol Chem 265:21128–21133.

MJ Lenardo et al (1989) Cell 58:227–229.

*Primary Examiner*—Bruce R. Campbell
*Attorney, Agent, or Firm*—Brinks Hofer Gilson & Lione

[57] ABSTRACT

Administration of a double-stranded DNA NF-κB inhibitor is effective for the treatment of immune and inflammatory diseases, cancer, and viral infections.

2 Claims, 7 Drawing Sheets

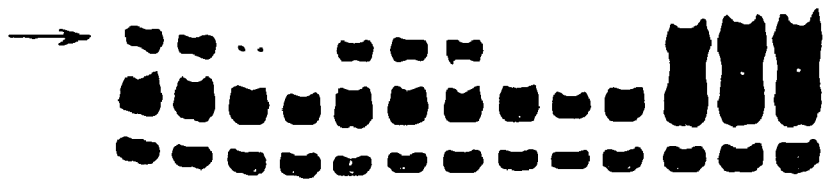
FIGURE 1

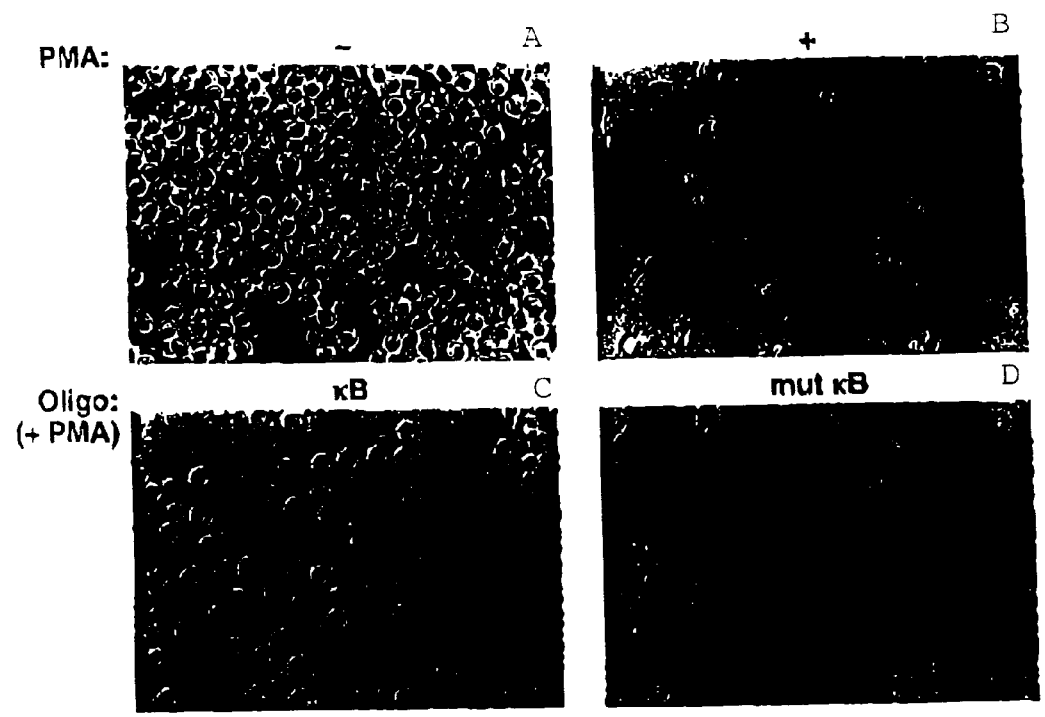
FIGURES 2A-D

PMA: − +
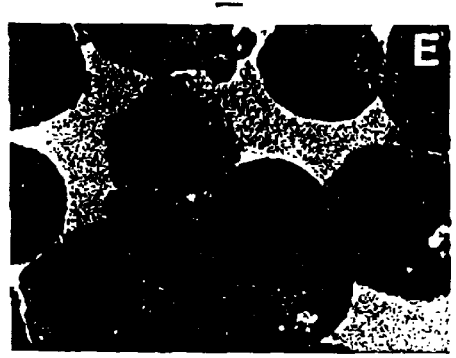 
Oligo: κB mut κB
(+ PMA)
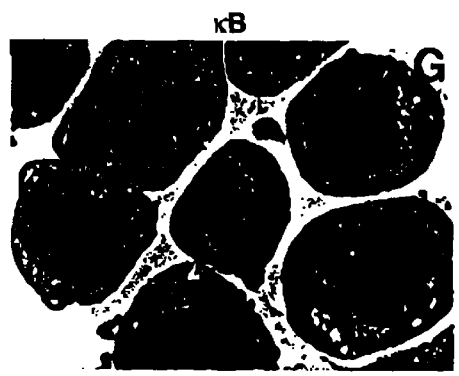 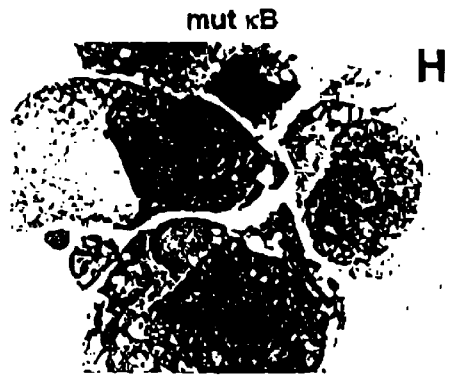
FIGURES 2E-H

METHODS AND COMPOSITIONS FOR TREATMENT OF DISEASES

This application continuation of application Ser. No. 08/123,188, filed on Sep. 20, 1993, now abandoned.

BACKGROUND OF THE INVENTION

1. Field of the Invention

The present invention relates to methods and compositions for treating immune and inflammatory diseases, cancer, and viral infections.

2. Discussion of the Background

Inflammatory diseases, such as rheumatoid arthritis, ischemia/reperfusion injury, restenosis, transplant rejection, poison ivy, poison oak, poison sumac, Crohn's disease, ulcerative colitis, psoriasis, and glomerulonephritis, are characterized by the expression of certain types of surface proteins which mediate cell adhesion. For example, in the case of transplant rejection, expression of cellular adhesion molecules such as ICAM-1, ELAM, or VCAM-1 is responsible for initiating the attachment of leukocytes and/or lymphocytes to post-capillary venules with subsequent migration into involved tissues. By interfering with this process, for example, it is possible to ameliorate local inflammation, cell proliferation and the immune response to inhibit the rejection response (see, e.g., Sadahiro, M. et al. *Am. J. Pathology,* 142:675–683 (1993)). A similar role has been suggested for VCAM-1 in the initiation of atherosclerosis or restenosis (Cybulsky, M. I. et al, *Science,* 251:788–799 1991)). Similar processes contribute to the inflammation observed in other diseases, including rheumatoid arthritis, Crohn's disease, and reperfusion injury.

Although there are treatments available for many of such inflammatory diseases, none is entirely satisfactory. Thus, there remains a need for methods and compositions for the treatment of inflammatory diseases. In particular, there remains a need for methods and compositions for treating rheumatoid arthritis, ischemia/reperfusion injury, restenosis, transplant rejection, poison ivy, poison oak, poison sumac, Crohn's disease, ulcerative colitis, psoriasis, and glomerulonephritis. There also remains a need for methods and compositions for the treatment of cancer and viral infections.

SUMMARY OF THE INVENTION

Accordingly, it is an object of the present invention to provide novel methods for the treatment of inflammatory disease.

It is another object of the present invention to provide methods for the treatment of rheumatoid arthritis.

It is another object of the present invention to provide methods for the treatment of ischemia/reperfusion injury.

It is another object of the present invention to provide methods for the treatment of restenosis.

It is another object of the present invention to provide methods for the treatment of transplant rejection.

It is another object of the present invention to provide methods for the treatment of poison ivy.

It is another object of the present invention to provide methods for the treatment of poison oak.

It is another object of the present invention to provide methods for the treatment of poison sumac.

It is another object of the present invention to provide methods for the treatment of Crohn's disease.

It is another object of the present invention to provide methods for the treatment of ulcerative colitis.

It is another object of the present invention to provide methods for the treatment of psoriasis.

It is another object of the present invention to provide methods for the treatment of glomerulonephritis.

It is another object of the present invention to provide methods for the treatment of cancer.

It is another object of the present invention to provide methods for the treatment of viral infections.

It is another object of the present invention to provide pharmaceutical compositions for the treatment of inflammatory diseases.

It is another object of the present invention to provide pharmaceutical compositions for the treatment of rheumatoid arthritis.

It is another object of the present invention to provide pharmaceutical compositions for the treatment of ischemia/reperfusion injury.

It is another object of the present invention to provide pharmaceutical compositions for the treatment of restenosis.

It is another object of the present invention to provide pharmaceutical compositions for the treatment of transplant rejection.

It is another object of the present invention to provide pharmaceutical compositions for the treatment of poison ivy.

It is another object of the present invention to provide pharmaceutical compositions for the treatment of poison oak.

It is another object of the present invention to provide pharmaceutical compositions for the treatment of poison sumac.

It is another object of the present invention to provide pharmaceutical compositions for the treatment of Crohn's disease.

It is another object of the present invention to provide pharmaceutical compositions for the treatment of ulcerative colitis.

It is another object of the present invention to provide pharmaceutical compositions for the treatment of psoriasis.

It is another object of the present invention to provide pharmaceutical compositions for the treatment of glomerulonephritis.

It is another object of the present invention to provide pharmaceutical compositions for the treatment of cancer.

It is another object of the present invention to provide pharmaceutical compositions for the treatment of viral infections.

These and other objects, which will become apparent during the following detailed description, have been achieved by the inventors' discovery that immune and inflammatory diseases, cancer and viral infections may be effectively treated by administration of a double-stranded NF-κB inhibitor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 illustrates double-stranded κB phosphorothioate oligonucleotide inhibition of the binding of NF-κB from HL-60 cell nuclear extracts. Electrophoretic mobility gel shift assays were performed using nuclear extract from PMA-stimulated HL-60 cells and varying concentrations of competitor as described in Materials and Methods section below. The NF-κB specific band is indicated by the arrow. ΔκB-PT, mut κB homolog; κB-DE, κB diester; Oct, oligonucleotide with multimerized octomer binding sites; –, control.

FIGS. 2A–H show κB-PT oligonucleotide specific inhibition of PMA-induced adhesion and morphological changes of HL-60 cells. (A–D): HL-60 cells were incubated with double-stranded phosphorothioate oligonucleotides (Oligo) or media control, for three hours followed by addition of PMA (+) or media (−) as indicated. Cells were photographed after 27 hours in culture. Magnification, 25×. (E to H): Wright's stained preparations of HL-60 cells showing morphological changes associated with PMA stimulation in the presence or absence of the κB-PT digonucleotide indicated. Cells were treated as described above. Magnification, ×1,000.

DETAILED DESCRIPTION OF THE PREFERRED EMBODIMENTS

Figure 3:
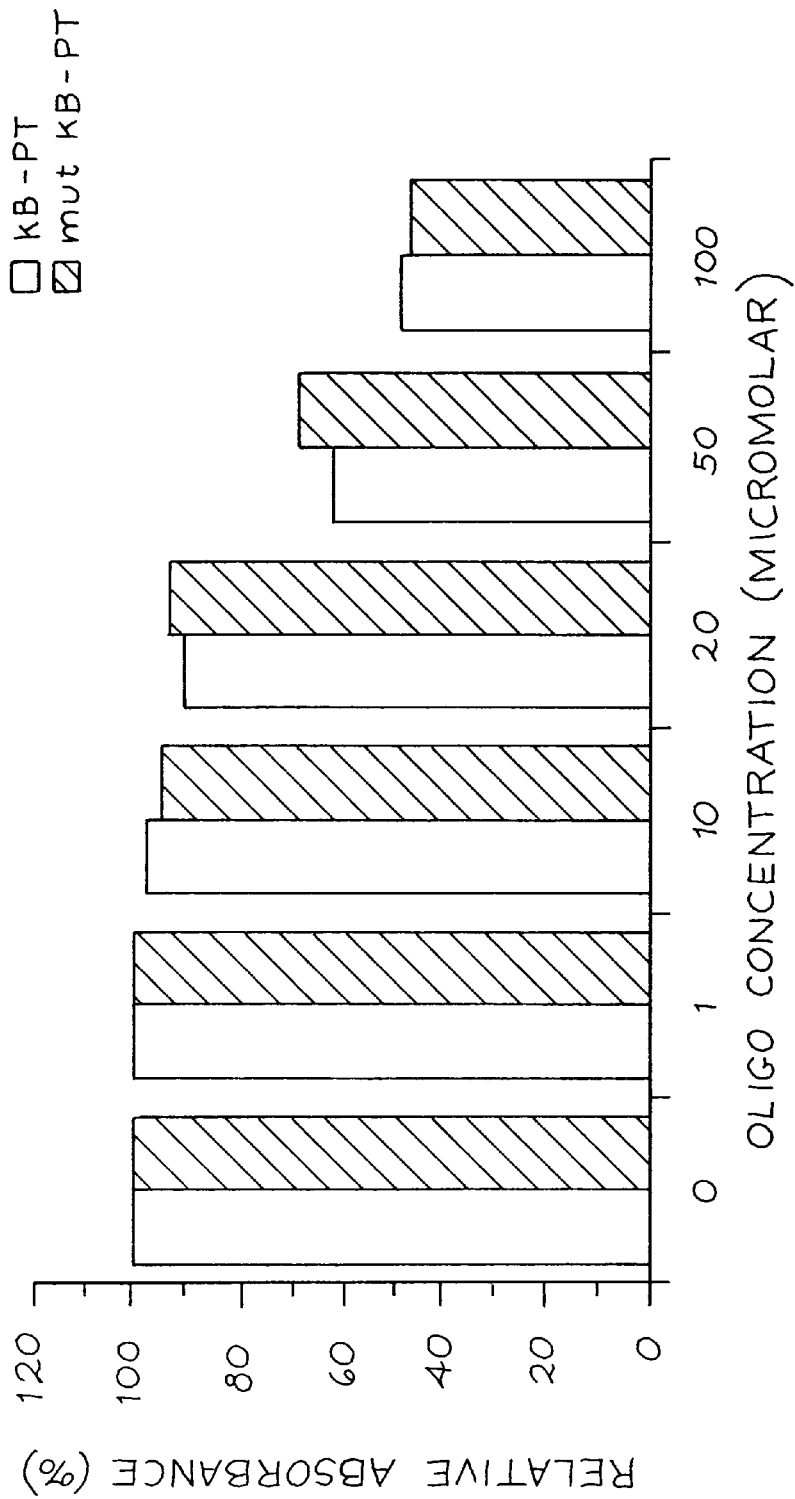
FIG. 3 shows the effect of double-stranded phosphorothioate oligonucleotides on HL-60 cell proliferation. HL-60 cells were incubated with the indicated double-stranded phosphorothioate oligonucleotides (solid bars–κB-PT; shaded bars–mutated κB-PT) at the concentrations shown for 48 hours. Cell proliferation was measured by the MTT assay (Loveland, B. E. et al, *Biochem. Int.*, 27:501–510 (1992))
Figure 4A:
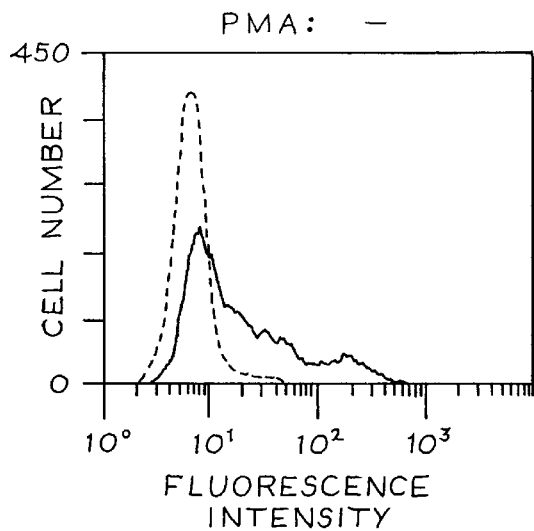
FIGS. 4A–D illustrate κB-PT oligonucleotide specific inhibition of PMA-induced CD11b expression in HL-60 cells. HL-60 cells were incubated with media alone (−) (panels A & B), κB-PT (panel C), or mut κB-PT (panel D) for 3 hours, followed by stimulation with PMA (+) (panels B, C & D) for 24 hours. After incubation with the relevant monoclonal and secondary fluorescent antibodies, cells were examined by flow cytometry. Solid curves, anti-CD11b; dashed curves, isotype control antibody; Oligo, oligonucleotide.
Figure 4B:
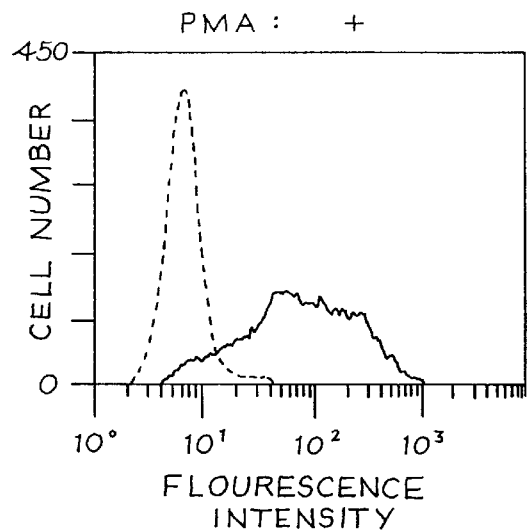
Figure 4C:
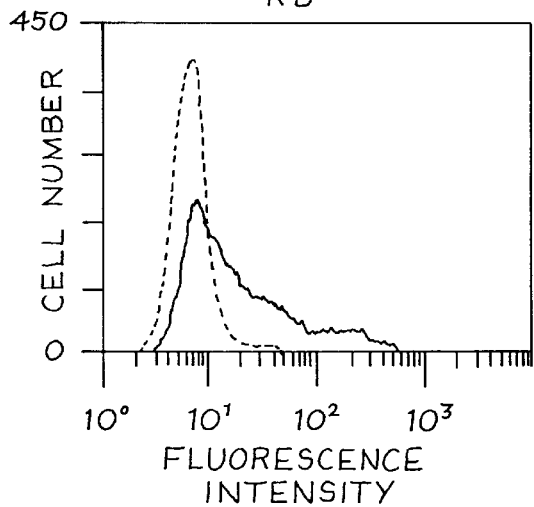
Figure 4D:
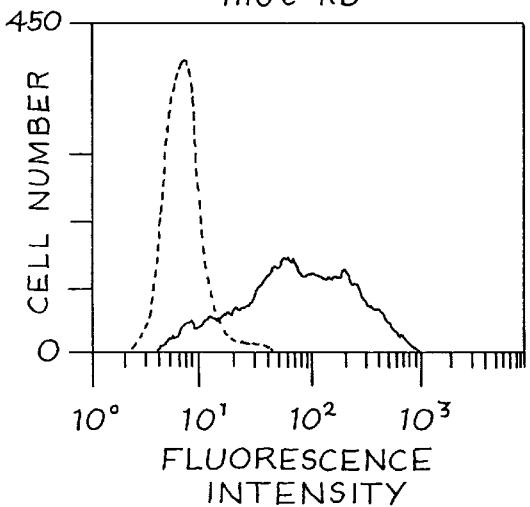
Figure 5A:
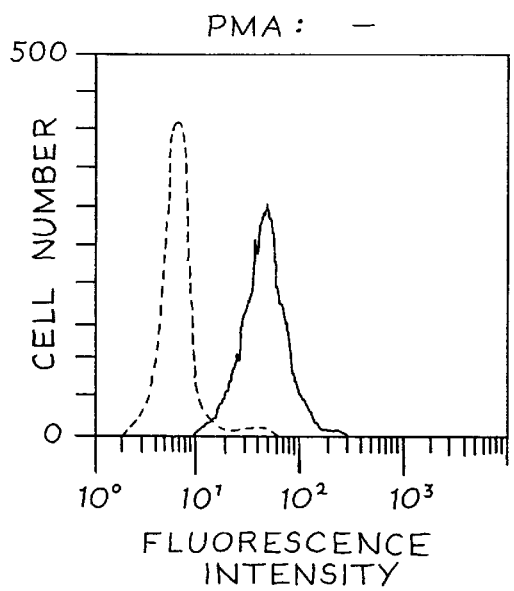
FIGS. 5A–D show that κB-PT oligonucleotide fails to inhibit CD18 expression in HL-60 cells. HL-60 cells were incubated with medium along (−) (A and B), κB-PT (C), or mut κB-PT (D) for 3 h, followed by 24 h of stimulation with PMA(+) (B to D). After incubation with the relevant monoclonal antibodies, cells were examined by flow cytometry. Solid curves, anti-CD18; dashed curves, isotype control antibody; Oligo, oligonucleotide.
Figure 5B:
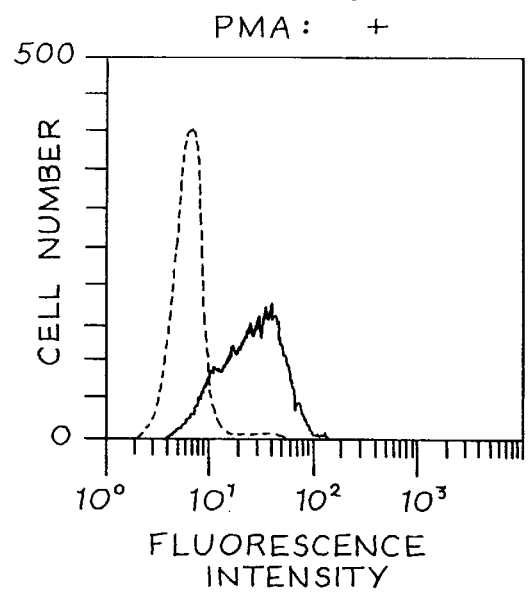
Figure 5C:
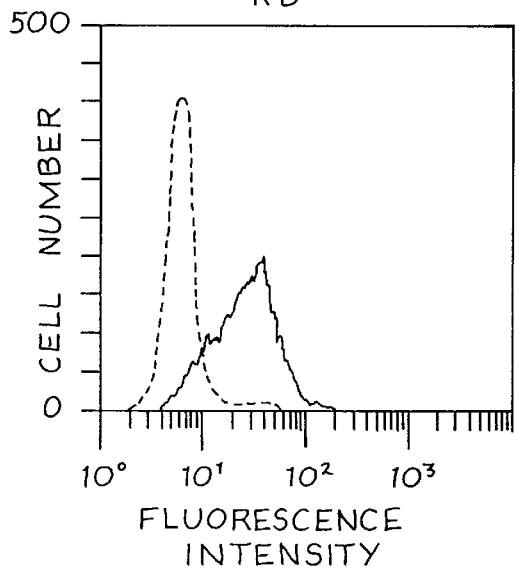
Figure 5D:
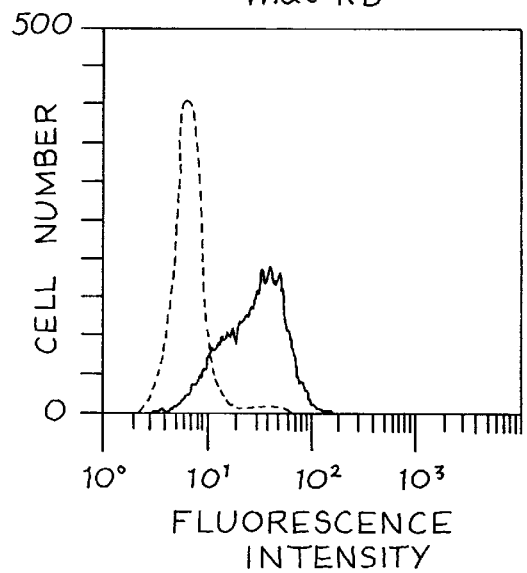
Figure 6A:
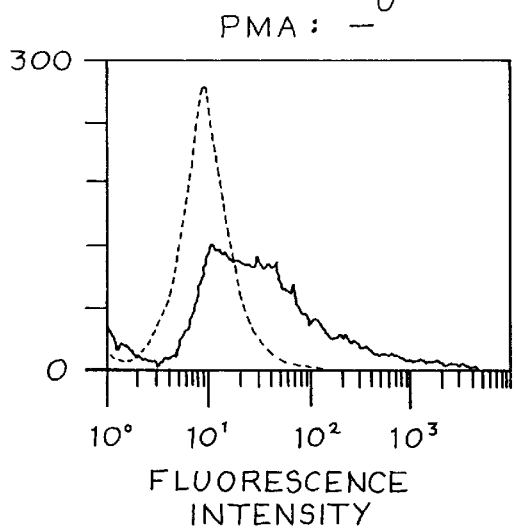
FIGS. 6A–D illustrate κB-PT oligonucleotide specific inhibition of PMA-induced ICAM expression in endothelial cells. Human endothelial cells were treated with κB-PT, mut κB-PT, or media alone (−) for 3 hours, followed by stimulation with PMA (+) for 4 hours. Anti-ICAM stained cells were analyzed by flow cytometry. Solid curves, anti-ICAM; dashed curves, isotype control antibody; Oligo, oligonucleotides.
Figure 6B:
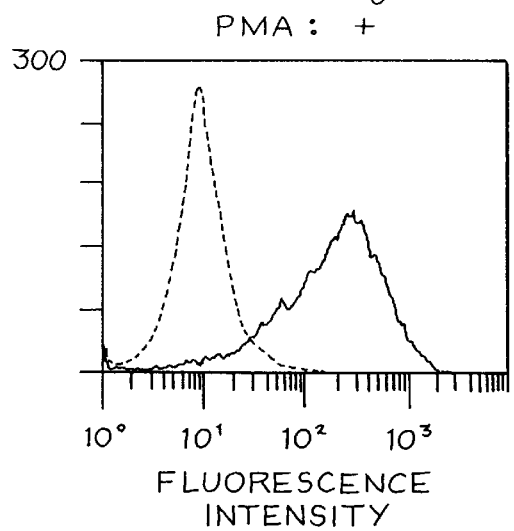
Figure 6C:
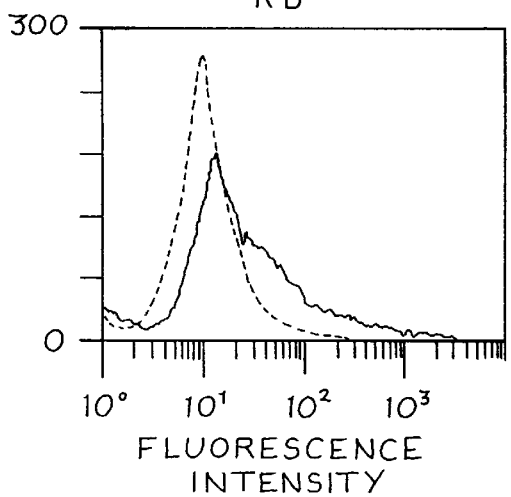
Figure 6D:
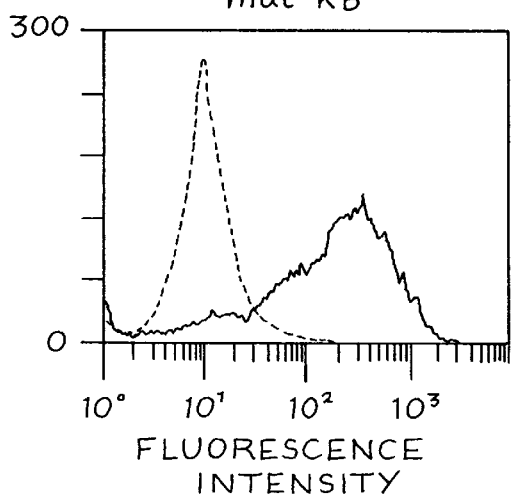

Thus, in a first embodiment, the present invention provides methods for treating inflammatory diseases. Specifically, the present methods comprise administering a double-stranded NF-κB inhibitor.

The double-stranded NF-κB inhibitors used in the present method are double stranded DNA molecules and include those in which the nucleoside residues are linked by phosphorothioate groups and methyl derivatives in addition to phosphate groups. Such linking groups have the formula

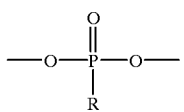

where R=O⁻, S⁻, OMe, and Me. The synthesis of all of these types of DNA is well within the abilities of the skilled artisan.

The preferred inhibitors are phosphorothioate DNAs in which R=S⁻. Such double-stranded phosphorothioate DNA molecules may be prepared by first synthesizing a single-stranded DNA oligonucleotide by conventional methods with, e.g., an automated DNA synthesizer and then reacting the single-stranded DNA digonucleotide with tetraethylthiuurinium disulfide. The single-stranded phosphorothioate so obtained may then be annealed with a complementary single-stranded phosphorothioate DNA.

Suitably, the double-stranded NF-κB inhibitor used in the present methods will be 14 to 40, preferably 25 to 38 nucleotide residues long and contain at least one nucleotide sequence which is at least 60 to 100%, preferably 90 to 100% identical to the sequence of formula (I)(SEQ ID NO:1)

as the sense strand. Preferably, the double-stranded NF-κB inhibitor contains a plurality of DNA sequences of formula (I) in the sense strand, which may be repeated one or more times in the sequence. In a particularly preferred embodiment, the inhibitor comprises a sequence of formula (II)(SEQ ID NO:2)

as the sense strand, in which the portions corresponding to the sequence of formula (I) (SEQ ID NO:1) are underlined.

Preferably, the double stranded NF-κB inhibitor used in the present invention has, as the sense strand, a nucleotide sequence which consists of the oligonucleotide of formula (I) (SEQ ID NO:1). Preferably, the two strands are perfectly complementary. It is also possible to make a single strand which is self complementary internally but contains a hairpin.

Although the present method may be used to treat any inflammatory disease, in preferred embodiments, the inflammatory disease is rheumatoid arthritis, ischemia/reperfusion injury, restenosis, transplant rejection, poison ivy, poison oak, poison sumac, Crohn's disease, ulcerative colitis, psoriasis, or glomerulonephritis. The present method may also be used to treat cancer. In particular, the present method may be used to treat leukemia, melanoma, sarcoma, and lymphomas including cutaneous T-cell lymphoma. The present method may also be used to treat viral infections. The present method may be used to treat both retroviral infections and DNA-viral infections. Examples of the viral infections which may be treated with the present method include herpesviruses, HTLV, and HIV.

The NF-κB inhibitor may be administered by conventional techniques, including by catheter, intravenously, subcutaneously, orally, endoscopically, intramuscularly, intra-articularly, as well as topical application. The preferred mode of administration will, of course, depend on the disease being treated. Thus, when psoriasis or a reaction to poison ivy, poison oak, or poison sumac is being treated, the preferred mode of administration will be topical application.

In the case of rheumatoid arthritis, intra-articular injection directly into the affected joint is preferred. In the case of restenosis, catheter-based delivery is preferred, while the agent is preferentially delivered orally or endoscopically for the inflammatory bowel diseases, Crohn's disease and ulcerative colitis. For glomerulonephritis intravenous injection is the preferred route of delivery. In the case of cancer and viral infections, oral or intravenous administration is preferred.

The NF-κB inhibitors may be administered in the form of any conventional composition suitable for the mode of administration being used. Thus, in the case of topical administration, the NF-κB inhibitor is preferably contained in an ointment, jelly, cream, lotion, etc. Such compositions may be either an oil-in-water or a water-in-oil emulsion. Alternatively, when the NF-κB inhibitor is to be administered by injection, the NF-κB is suitably contained in a sterile solution or suspension. Suitable ingredients and procedures for forming suitable pharmaceutical compositions are disclosed in Kirk-Othmer, Encyclopedia of *Chemical Technology*, 3rd ed., Wiley, New York, vol. 17, pp. 272–310 (1982), which is incorporated herein by reference. In the case of catheter delivery, this agent may be best delivered together with cationic liposomes, including those previously approved for use in humans (Gao et al, *Biochem. Biophys. Res. Commun.*, (1992); Nabel et al, *Proc. Natl. Acad. Sci. USA*, in press (1993)) or with biodegradable gels or fibrin clots. Such formulations may also be used in the treatment of rheumatoid arthritis or inflammatory bowel disease.

In some cases, it may be preferred to coadminister the NF-κB inhibitor of the present invention along with an inhibitor of another transcriptional factor. For example, in the treatment of HIV-1 infection, it may be preferred to coadminister a binding inhibitor of SP1 (see: Perkins, N. D. et al, *EMBO Journal*, 12:3551–3558 (1993)). In the treatment of HIV-1 and cancer, it may be preferred to coadminister a binding inhibitor of a Rel oncoprotein (see: Sif, S. et al, *Oncogene*, 8:2501–2509 (1993); Morin, P. J. et al, *Nucleic Acids Res.*, 21:2157–2163 (1993); Sarkar, S. et al, *Oncogene*, 8:2245–2252 (1993)). It should be understood that the other inhibitor being coadministered with the NF-κB inhibitor may be either a separate distinct molecule or may be a sequence of DNA which is contained in a larger sequence of DNA which also contains the NF-κB inhibitor. For example, in a preferred embodiment, a single sequence of DNA will contain both the NF-κB inhibitor and a SP1 binding inhibitor.

The NF-κB inhibitor may also be covalently linked to other types of molecules. For example, the NF-κB inhibitor may be covalently linked to either a polypeptide and/or monoclonal antibody to target the inhibitor to a particular cell and/or the nucleus.

The exact dosage range of the NF-κB inhibitor to be administered will depend on the disease being treated and the size and condition of the patient. However, the dosage of NF-κB inhibitor is suitably 1 to 20 cc, preferably 5 to 10 cc, of a suitably 1 to 100 μM, preferably 1 to 20 μM, solution of the inhibitor, in the case of rheumatoid arthritis; suitably 5 to 50 cc, preferably 10 to 30 cc, of a suitably 1 to 10 μM, preferably 1 to 20 μM, solution of the inhibitor, in the case of ischemia/reperfusion injury; suitably 0.5 to 10 cc, preferably 1 to 5 cc, of a suitably 1 to 100 μM, preferably 1 to 20 μM, solution of the inhibitor in the case of restenosis; suitably 1 to 10 cc, preferably 3 to 5 cc, of a suitably 1 to 100 μM, preferably 1 to 20 μM, solution of the inhibitor, in the case of poison ivy, oak, or sumac or psoriasis; suitably 10 to 100 cc, preferably 25 to 75 cc, of a suitably 1 to 100 μM, preferably 1 to 20 μM, solution of the inhibitor, in the case of Crohn's disease or ulcerative colitis; and suitably 5 to 50 cc, preferably 10 to 40 cc, of a suitably 1 to 100 μM, preferably 1 to 20 μM, solution of the inhibitor, in the case of glomerulonephritis.

In the case of cancer, the dosage is suitably 10 to 200 cc, preferably 50 to 100 cc, of a 1 to 100 μM, preferably 1 to 20 μM, solution of the inhibitor. In the case of a viral infection, the dosage is suitably 10 to 200 cc, preferably 50 to 100 cc, of a 1 to 100 μM, preferably 1 to 20 μM, solution of the inhibitor.

In the Examples given below, the role of NF-κB in cell adhesion was examined utilizing a human promyelocytic leukemia cell line (HL-60 cells). HL-60 can be induced to differentiate into monocytoid cells by treatment with phorbol esters, with concomitant expression of the leukocyte adhesion glycoprotein CD11b. CD11b when non-covalently complexed with CD18, forms the integrin Mac-1. Through their leukocyte-limited expression CD11b/CD18 mediate adhesion to other cells, insoluble ligands following complement activation or clotting cascades (Kishimoto, T. K. et al, *Adv. Immunol.*, 46:149–182 (1989), and likely participate in adhesion to plastic surfaces. Individuals lacking CD11b/CD18 suffer from recurrent infections as a result of defective granulocytic function (Todd, R. D., III et al, *Hematol. Oncol. Clin. North. Am.*, 2:13–31 (1988). Furthermore, autoantibodies to the glycoprotein complex CD11b/CD18 have been shown to be present in patients with autoimmune neutropenia (Hartman, K. R. et al, *Blood*, 78:1096–1104 (1991)).

In the Examples, it is demonstrated that a phosphorothioate modified double-stranded oligonucleotide containing multiple κB sequences (κB-PT) can specifically bind NF-κB from HL-60 cell nuclear extracts (FIG. 1). HL-60 cells were incubated with κB-PT, or its mutated congener (mut κB-PT). In the absence of PMA, the oligonucleotides had no effect on cell growth and viability (FIG. 3). However, PMA stimulation following κB-PT treatment, failed to induce differentiation (FIG. 2C). The cells did not adhere to the plastic tissue culture dish and maintained their pretreatment morphology. In contrast, the cells treated with PMA alone, or sequentially with mut κB-PT and PMA became adherent to, and spread along the plastic surface, which is characteristic of HL-60 cell differentiation (FIG. 2, B and D). CD11b expression occurs in synchrony with these morphologic changes and can be detected by FACS analysis 20 hours after exposure to PMA. The appearance of CD11b was inhibited by pretreatment with κB-PT, but not by mut κB-PT (FIG. 4) in concert with the observed morphologic appearance. When cycloheximide or α-amanitin was employed prior to PMA treatment, CD11b induction at 24 hours was abolished (FIG. 5). Taken together, these findings suggest that the process of differentiation in HL-60 cells requires new transcriptional events which are dependent, at least in part, on NF-κB.

Transcriptional activation requires the interaction of many constitutive and conditional factors, and it seems likely that NF-κB plays an integral role in this process. The 5' regulatory region of the CD11b gene has recently been characterized (Hickstein, D. D. et al, *Proc. Natl. Acad. Sci. USA*, 89:2105–2109 (1992); Pahl, H. L. et al, *Blood*, 79:865–870 (1992)) and does not appear to contain κB elements. CD11b appears on the cell surface within a few hours after stimulation with PMA. Hickstein et al observed an enhancement of the steady state level of CD11b message in the absence of any apparent increase in the transcription rate. They postulate that CD11b is likely post-transcriptionally regulated in response to PMA, but may be transcriptionally regulated in response to cytokines (Hickstein, D. D. et al, *J. Biol. Chem.*, 264:21812–21817 (1989)).

Like HL-60 cells, human endothelial cells can be induced to express adhesion molecules following PMA stimulation. ICAM-1 appears on the cell surface within a few hours following exposure to PMA. When HUVECs were incubated with κB-PT prior to PMA stimulation, ICAM expression was inhibited, while the mut κB-PT oligonucleotide had no effect (FIG. 6). PMA induction of ICAM-1 was also inhibited by pretreatment with actinomycin D, α-amanitin, or cycloheximide (FIG. 7) as has been reported previously (Wertheimer, S. J. et al, J. Biol. Chem., 267:12030–12035 (1992).

The double-stranded phosphorothioate oligonucleotide containing multiple copies of the immunoglobulin κB sequence (κB-PT) is taken up by cells, binds activated NF-κB, and thus prevents NF-κB binding to endogenous κB enhancer/promoter elements. Thus, e.g., in human umbilical vein endothelial cells (HUVEC) and HL-60 cells, the PMA induced expression of proteins mediating cell adhesion can be specifically inhibited by oligonucleotides which bind to NF-κB. These results substantiate the role of NF-κB in the induction of cell adhesion associated with differentiation or activation.

DNA which is antisense to the p65 subunit of NF-κB inhibits the growth of HTLV-I transformed tumors in nude mice (Kitajima, I. et al, Science, 258:1792–1795 (1992)). The $tax_1$gene of HTLV-I induces NF-κB (Leung, K. et al, Nature, 333:776–778 (1988)), and there is a rearrangement of one form of NF-κB, NF-κB2, in certain B cell leukemias (Neri, A. et al, Cell, 67:1075–1087 (1992)). Thus, the present double-stranded inhibitors may be used as anticancer and/or anti-viral agents.

Other features of the invention will become apparent in the course of the following descriptions of exemplary embodiments which are given for illustration of the invention and are not intended to be limiting thereof.

EXAMPLES

I. MATERIALS AND METHODS

A. Phosphorothioate Oligonucleotides

Single-stranded oligonucleotides were synthesized on an automated synthesizer using tetraethylthiurinium disulfide as the phosphorus oxidant (Applied Biosystems User Bulletin, #58, February 1991, Applied Biosystems, Foster City, Calif.). The oligonucleotides were purified by denaturing polyacrylamide gel electrophoresis (Sambrook, J. et al, Molecular cloning, A Laboratory Manual, Cold Spring Harbor Laboratory, Cold Spring Harbor, N.Y., 1989), or on a Poly-Pak cartridge (Glen Research, Sterling, Va.) according to the manufacturer's protocol. Following quantification by absorbance at 260 nm, equimolar amounts of complementary strands were annealed in 0.5 M NaCl. The oligonucleotide sequences were as previously described (Bielinska, A. et al, Science, 250:997–1000 (1990)). The κB-PT sequence is GGGGACTTTCCGCTGGG-GACTTTCCAGGGGGACTTTCC (SEQ ID NO: 2) hybridized to its reverse complement. The mutated κB-PT (mut κB-PT) is: GTCTACTTTCCGCTGTCTACTTTCCACG-GTCTACTTTCC, (SEQ ID NO. 3) hybridized to its reverse complement. Phosphodiester oligonucleotides were synthesized by standard methods.

B. Cell Culture

Primary endothelial cells were harvested from human umbilical cord veins, as previously described (Huber, A. R. et al, J. Clin. Invest., 83:1122–1136 (1989)), or obtained from Clonetec (Pala Alto, Calif.) and grown on gelatin-coated dishes. Cells from third to fifth passage were used. HL-60 cells were obtained from the American Type Culture Collection (ATCC), grown in RPMI with 10% fetal calf serum supplemented with glutamine (2 mM), penicillin G (50 U/ml) and streptomycin (50 µg/ml), and used at random passages.

Cells were treated with the oligonucleotides (20 µM) in a minimal volume of media (0.5 ml) in six-well plastic tissue culture dishes for 3 hours followed by incubation with PMA (20 ng/ml) for 4 hours (HUVECs), 24 hours (HL-60 cells), or as indicated. Cells were harvested by trypsinization (HUVECs) or by gentle scraping (HL-60 cells) and washed with phosphate-buffered saline (PBS).

C. Fluorescence-Activated Cell Sorter (FACS) Analysis

Harvested cells were incubated on ice, in PBS containing 0.01% $NaN_3$, for 1–2 hours with monoclonal antibodies (AMAC, Westbrook, Me.) to intercellular adhesion molecule-1 (ICAM-1) (1:50 dilution), CD11b (1:100 dilution), CD18 (1:50 dilution), or isotype control. They were washed twice with $PBS/NaN_3$ followed by second antibody staining (goat anti-mouse fluorescein isothiocyanate-labeled antibody, Sigma Chemical Co.) for 1–2 hours in the dark. The anti-CD18 antibody was conjugated to fluorescein isothiocyanate and thus did not require treatment with the secondary antibody. After washing twice with $PBS/NaN_3$, cell associated fluorescence was determined on a Becton Dickinson fluorescence activated cell sorter (FACSCAN).

D. Electrophoretic Mobility Shift Assays

Gel shift assays were performed as previously described (Schmid, R. M. et al, Nature, 352:733–736 (1991).

E. MTT Cellular Proliferation Assay

MTT assays (Loveland, B. E. et al, Biochem. Int., 27:501–510 (1992)) were performed by incubating 50 µl of HL-60 cells (200,000 cells per ml) with 50 µl of oligonucleotides at various concentrations. After 24 hours, 0.01 ml of sterile filtered 3-(4,5-dimethylthiazol-2-yl) -2,5-diphenyltetrazolium bromide (MTT, Sigma Chemical Co.) at a concentration of 5 mg/ml in PBS was added. Cells were incubated at 37° C. for 4 hours. Acidic isopropanol (0.04 M HCl in isopropnaol) (0.1 ml) was added with thorough mixing. $A_{570}$ (MTT formation) was compared with $A_{767}$ (control).

F. Wright's Stain

HL-60 cells were washed once with $PBS-NaN_3$ and then spun onto glass slides (500 rpm for 10 minutes) on a Cytospin centrifuge (Shandon Corp.). The air-dried slides were stained with modified Wrights stain (Sigma Chemical Co.) according to the manufacturers protocol. Cells were photographed under oil immersion at a magnification of ×,1,000.

II. RESULTS

A. κB Phosphorothioates Inhibit NF-κB Binding in HL-60 Cell Nuclear Extracts

The phenotypic differentiation of monocyte cell lines, induced by phorbol esters, is associated with induction of NF-κB activity, with concomitant transcriptional activation of NF-κB dependent transcription (Griffin, G. E. et al, Nature, 339:70–73 (1989)). In order to demonstrate that double-stranded oligonucleotides containing κB binding sequences could bind endogenous NF-κB from HL-60 cells, electrophoretic mobility gel shift assays (EMSA) with nuclear extracts (Dignam, J. D. et al, Nucl. Acids Res., 11:1475–1489 (1983)) from PMA-treated HL-60 cells were performed (FIG. 1). The κB-PT oligonucleotide, (SEQ ID NO:2) containing three multimerized κB sequences, (lanes κB-PT) specifically inhibited NF-κB binding in a dose dependent manner. The mutated κB homologue (SEQ ID NO:3) (lanes FIG. 1, lanes ΔκB-PT) or an oligonucleotide with multimerized octamer binding sites (lanes Oct), did not inhibit binding to the κB diester oligonucleotide probe. A κB diester oligonucleotide competitor (SEQ ID NO:2) similarly inhibited NF-κB binding (FIG. 1, lanes κB-DE). The slight difference in efficiencies of competition (two- to five-fold) between the diester oligonucleotide and the phosphorothioate analog (compare lanes κB-PT[1 ng] and κB-DE [1 ng] of FIG. 1) was consistently observed, although in varying degrees, and may reflect a larger disassociation constant for the phosphorothioate analogs. This result demonstrates that phosphorothioate- modified double-stranded oligonucleotides with multiple κB elements can bind specifically to cellular NF-κB and therefore may be used to affect the targets of this transcription factor in vivo.

B. Inhibition of PMA-Induced HL-60 Cell Differentiation By Double-Stranded κB Phosphorothioates HL-60 cells, on treatment with PMA, differentiate into cells with phenotypic appearance of macrophages and the expression of new cell surface proteins, including CD11b (Pedrinaci, S. et al, *Hybridoma*, 8:13–23 (1989). The effect of κB-PT oligonucleotides on PMA stimulation of HL-60 cells was investigated by incubating the cells with κB-PT (SEQ ID NO:2)(20 μM), mutated κB-PT (SEQ ID NO: 3) (20 μM), or media alone, for 3 hours prior to stimulation with PMA (20 ng/ml) for 24 hours. The cells induced by PMA which were pretreated with κB-PT (SEQ ID NO:2) retained the phenotype appearance of unstimulated cells (FIG. 2; A vs. C). In contrast, the PMA-induced HL-60 cells treated with Mut κB-PT (SEQ ID NO:3) were phenotypically identical to the cells treated with PMA alone (FIG. 2, B vs. D). More specifically, the cells treated with κB-PT (SEQ ID NO:2) retained their high nucleus to cytoplasm ratio and diffuse nuclear chromatin, as seen in the untreated cells (FIG. 2; E and G). In contrast, the PMA-induced cells incubated with the mut κB-PT (SEQ ID NO:3) showed a decline in nuclear-to-cytoplastic ratio, clumping of nuclear chromatin, less prominent nucleoli, and more lysosomal granules identical to the PMA-induced control cells in the absence of oligonucleotides (cf. FIG. 2; F H.) In addition, cellular proliferation, which is arrested by PMA treatment, continued in cells treated with κB-PT (SEQ ID NO:2) and PMA (data not shown). When κB-PT oligonucleotide (SEQ ID NO:2)treated HL-60 cells were removed from culture after 24 hours and incubated with fresh media for 72 hours, no inhibition of PMA induced morphologic change was observed (data not shown). At the concentrations used to demonstrated these effects, neither κB-PT (SEQ ID NO:2) or mut κB-PT (SEQ ID NO:3) affected the viability of unstimulated cells as judged by trypan blue staining or by cell proliferation (MTT) assay (FIG. 3), indicating that these effects were not secondary to toxicity of these compounds. At higher concentrations of oligonucleotides, a slight diminution in cell proliferation was observed. Concentrations of oligonucleotides less than or equal to 10 μM had no effect. A minimum of 3 hours of preincubation with oligonucleotides at a concentration of 20 μM was required.

The cell surface glycoprotein, CD11b, appears on HL-60 cells following PMA stimulation concomitant with phenotypic differentiation. The appearance of this protein was measured by FACS analysis after treatment of cells with κB-PT (20 μM) for three hours, followed by incubation with PMA for an additional 24 hours. The κB-PT (SEQ ID NO:2) double-stranded oligonucleotide inhibited the induction of CD11b expression caused by PMA (FIG. 4, A vs. C). In contrast, the mut κB-PT double-stranded oligonucleotide (SEQ ID NO:3) did not affect CD11b induction (FIG. 4, B vs. D). In parallel with these experiments, the expression of CD18, which naturally complexes with CD11b on HL-60 cells to form the Mac-1 integrin, was also analyzed. As in previous reports (Hickstein, D. D. et al, *J. Immunol.*, 138:513–519 (1987), CD18 was found to be expressed consitutively on HL-60 cells and, unlike Cd11b, was not inhibited by incubation with κB-PT oligonucleotide in the presence of PMA treatment (FIG. 5). These data demonstrate the specificity of CD11b inhibition by κB-PT.

C. Double-Stranded κB Phosphorothioates Inhibit ICAM Expression on Endothelial Cells Although fully differentiated, endothelial cells can also be activated to express cellular adhesion molecules (Shu, H. G., et al., *Mol. Cell. Biol.*, 13: (1993)), including ICAM-1. Treatment with agents such as PMA and cytokines (Hickstein, D. D., et al., *J. Biol. Chem.*, 264:21812–21817 (1989)), which are known to activate NF-κB (Baeuerle, P. A., *Biochimica et Biophysica Acta*, 1072:63–80 (1991)), stimulates their expression. The ICAM-1 gene contains κB elements in its promoter/enhancer region which contribute to inducible expression (Most, J., et al., *J. Immunol.*, 148:1635–1642 (1992); Stade, B. G., et al., *Immunobiol.*, 182:79–87 (1990)). Whether inhibition of NF-κB DNA binding activity in vivo could affect PMA-induced ICAM expression was investigated. Human umbilical vein endothelial cells (HUVECs) were incubated with κB-PT (SEQ ID NO:2) or mutated κB-PT (SEQ ID NO:3)(20 μM) for 2 hours, followed by another 3 hours of PMA stimulation (20 ng/ml). Treatment with κB-PT (SEQ ID NO:2) oligonucleotide, but not the mutated κB-PT (SEQ ID NO:3) inhibited PMA-induced ICAM expression as determined by flow cytometry (FIG. 6).

All references cited in this application are incorporated herein by reference. obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by: Letters Patent of the United States is:

1. A composition comprising a double stranded DNA NF-κB inhibitor comprising SEQ ID NO: 2 in the sense strand, and a pharmacologically acceptable carrier.

2. A composition comprising a double stranded DNA NF-κB inhibitor consisting of SEQ ID NO: 2 in the sense strand, and a pharmacologically acceptable carrier.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: both -continued

```
         (D) TOPOLOGY: linear (ii) MOLECULE TYPE: Other nucleic acid;
         (A) DESCRIPTION: SYNTHETIC DNA (ix) FEATURE:
         (A) NAME/KEY: misc_difference
         (B) LOCATION: replace(1..10, "")
         (D) OTHER INFORMATION: /note= "ANY OF THE PHOSPHATE GROUPS
             LINKING ANY OF THE NUCLEOSIDES MAY BE REPLACED
             WITH PHOSPHOROTHIOATE GROUPS, METHYL ESTER (xi) SEQUENCE DESCRIPTION: SEQ ID NO:1:

GGGACTTTCC                                                              10

(2) INFORMATION FOR SEQ ID NO:2:

(i) SEQUENCE CHARACTERISTICS:
        (A) LENGTH: 38 base pairs
        (B) TYPE: nucleic acid
        (C) STRANDEDNESS: both
        (D) TOPOLOGY: linear (ii) MOLECULE TYPE: Other nucleic acid;
         (A) DESCRIPTION: SYNTHETIC DNA (ix) FEATURE:
         (A) NAME/KEY: misc_difference
         (B) LOCATION: replace(1..38, "")
         (D) OTHER INFORMATION: /note= "ANY OF THE PHOSPHATE GROUPS
             LINKING ANY OF THE NUCLEOSIDES MAY BE REPLACED
             WITH PHOSPHOROTHIOATE GROUPS, METHYL ESTER (xi) SEQUENCE DESCRIPTION: SEQ ID NO:2:

GGGGACTTTC CGCTGGGGAC TTTCCAGGGG GACTTTCC                                38

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: both
        (D) TOPOLOGY: linear (ii) MOLECULE TYPE: Other nucleic acid;
         (A) DESCRIPTION: SYNTHETIC DNA (ix) FEATURE:
         (A) NAME/KEY: misc_difference
         (B) LOCATION: replace(1..39, "")
         (D) OTHER INFORMATION: /note= "ANY OF THE PHOSPHATE GROUPS
             LINKING ANY OF THE NUCLEOSIDES MAY BE REPLACED
             WITH PHOSPHOROTHIOATE GROUPS, METHYL ESTER (xi) SEQUENCE DESCRIPTION: SEQ ID NO:3:

GTCTACTTTC CGCTGTCTAC TTTCCACGGT CTACTTTCC                               39
```